United States Patent
Boukhny et al.

(10) Patent No.: US 9,149,340 B2
(45) Date of Patent: Oct. 6, 2015

(54) DISPLAY FOR OPHTHALMIC SURGICAL CONSOLE WITH USER-SELECTABLE SECTORS

(75) Inventors: Mikhail Boukhny, Laguna Niguel, CA (US); Raphael Gordon, Ladera Ranch, CA (US); Alexander N. Artsyukhovich, San Juan Capistrano, CA (US); Craig Gary Wooldridge, Irvine, CA (US); Tiffany Marie Sutliff, Fullerton, CA (US)

(73) Assignee: ALCON RESEARCH, LTD., Fort Worth, TX (US)

(*) Notice: Subject to any disclaimer, the term of this patent is extended or adjusted under 35 U.S.C. 154(b) by 382 days.

(21) Appl. No.: 13/086,509

(22) Filed: Apr. 14, 2011

(65) Prior Publication Data

US 2011/0257638 A1 Oct. 20, 2011

Related U.S. Application Data

(60) Provisional application No. 61/324,096, filed on Apr. 14, 2010.

(51) Int. Cl.
*A61B 19/00* (2006.01)
*A61F 9/007* (2006.01)
*A61F 9/008* (2006.01)

(52) U.S. Cl.
CPC ............ *A61B 19/52* (2013.01); *A61B 19/5225* (2013.01); *A61B 19/56* (2013.01); *A61B 19/5223* (2013.01); *A61B 19/5244* (2013.01); *A61B 2019/507* (2013.01); *A61B 2019/5227* (2013.01); *A61B 2019/568* (2013.01); *A61F 9/007* (2013.01); *A61F 9/008* (2013.01)

(58) Field of Classification Search
CPC ........ A61B 19/50; A61B 19/52; A61B 19/56; A61B 19/5225; A61B 2009/501; A61B 2009/507; A61F 9/00; A61F 9/007
USPC ........ 606/4–6, 10–12; 351/205–212; 128/898
See application file for complete search history.

(56) References Cited

U.S. PATENT DOCUMENTS

| | | | |
|---|---|---|---|
| 4,544,243 A | 10/1985 | Munnerlyn | |
| 4,591,247 A | 5/1986 | Kamiya et al. | |
| 4,870,964 A | 10/1989 | Bailey, Jr. et al. | |
| 5,028,802 A | 7/1991 | Webb et al. | |

(Continued)

FOREIGN PATENT DOCUMENTS

| | | |
|---|---|---|
| JP | 04170952 H | 6/1992 |
| JP | 2006136714 A | 6/2006 |

(Continued)

OTHER PUBLICATIONS

International Search Report for PCT/US2011/032432, 2 pages.

(Continued)

*Primary Examiner* — Ahmed Farah
(74) *Attorney, Agent, or Firm* — Jason Finch

(57) ABSTRACT

An ophthalmic surgical system includes a display device and a user interface. The display device generates a display on an image of a patient's eye comprising a plurality of non-overlapping display sectors. Each display sector displays one of a plurality of user-selectable surgical parameters. A user interface receives a user selection of one or more of the user-selectable surgical parameters to be displayed.

18 Claims, 4 Drawing Sheets

(56) References Cited

U.S. PATENT DOCUMENTS

| | | | |
|---|---|---|---|
| 5,098,426 A * | 3/1992 | Sklar et al. .................. 606/5 |
| 5,206,672 A | 4/1993 | Rowe |
| 5,303,085 A | 4/1994 | Rallison |
| 5,308,355 A | 5/1994 | Dybbs |
| 5,450,143 A | 9/1995 | Rowe et al. |
| 5,549,597 A | 8/1996 | Shimmick et al. |
| 5,619,377 A | 4/1997 | Rallison |
| 5,642,227 A | 6/1997 | Rallison |
| 5,673,151 A | 9/1997 | Rallison |
| 5,674,233 A | 10/1997 | Dybbs |
| 5,969,791 A | 10/1999 | Rowe |
| 5,991,087 A | 11/1999 | Rallison |
| 6,055,458 A * | 4/2000 | Cochran et al. ............ 700/17 |
| 6,066,129 A | 5/2000 | Larson |
| 6,078,681 A | 6/2000 | Silver |
| 6,087,941 A | 7/2000 | Ferraz |
| 6,149,643 A | 11/2000 | Herekar et al. |
| 6,159,205 A | 12/2000 | Herekar et al. |
| 6,193,710 B1 | 2/2001 | Lemberg |
| 6,394,999 B1 | 5/2002 | Williams et al. |
| 6,485,413 B1 | 11/2002 | Boppart et al. |
| 6,491,686 B2 | 12/2002 | Lemberg |
| 6,623,429 B2 | 9/2003 | Percival et al. |
| 6,669,340 B2 | 12/2003 | Percival et al. |
| 6,726,625 B2 | 4/2004 | Luce |
| 6,749,302 B2 | 6/2004 | Percival et al. |
| 6,816,316 B2 | 11/2004 | Caudle et al. |
| 6,908,196 B2 | 6/2005 | Herekar et al. |
| 6,945,650 B2 | 9/2005 | Beverly |
| 7,022,119 B2 | 4/2006 | Hohla |
| 2003/0159141 A1 | 8/2003 | Zacharias |
| 2004/0059321 A1 * | 3/2004 | Knopp et al. ............ 606/10 |
| 2004/0102799 A1 | 5/2004 | Perez et al. |
| 2005/0277913 A1 | 12/2005 | McCary |
| 2006/0247659 A1 | 11/2006 | Moeller et al. |
| 2008/0123183 A1 | 5/2008 | Awdeh |
| 2009/0048587 A1 * | 2/2009 | Avanzino et al. ........... 606/10 |
| 2009/0048608 A1 | 2/2009 | Boukhny et al. |
| 2009/0054879 A1 * | 2/2009 | Berry ........................ 606/5 |
| 2009/0225060 A1 | 9/2009 | Rizoiu et al. |
| 2009/0247997 A1 | 10/2009 | Watanabe et al. |
| 2009/0306581 A1 | 12/2009 | Claus |
| 2013/0088414 A1 * | 4/2013 | Artsyukhovich et al. ......... 345/7 |

FOREIGN PATENT DOCUMENTS

| | | |
|---|---|---|
| JP | 2007054423 A | 3/2007 |
| WO | 9009141 A | 8/1990 |

OTHER PUBLICATIONS

Written Opinion of the International Searching Authority, International Application No. PCT/US2011/032432, Jun. 30, 2011, 5 pages.
JPH04503913; English Abstract Only from corresponding WO9009141A3, no JP patent document available.

* cited by examiner

US 9,149,340 B2

DISPLAY FOR OPHTHALMIC SURGICAL CONSOLE WITH USER-SELECTABLE SECTORS

RELATED APPLICATIONS

This application claims priority under 35 USC §119 to U.S. provisional application Ser. No. 61/324,096, filed on Apr. 14, 2010.

TECHNICAL FIELD

This application relates to ophthalmic surgical devices and, more particularly, to a display for an ophthalmic surgical console with user-selectable sectors.

BACKGROUND

Various displays have been provided for ophthalmic surgical consoles. Such displays may frequently be overlaid on the surgical microscope used to view the eye. Unfortunately, these displays frequently suffer from several drawbacks. First, the displays can often be inconveniently placed, obscuring the surgeon's view of the eye and creating a tradeoff between the additional information provided in the display and clear vision of the surgical field. Second, including additional information in the display can make the display crowded and less usable. Third, the displays frequently use ring-shaped patterns, often including measurement scales. Such patterns can be distracting to the surgeon without being sufficiently visible for the surgeon to easily use them. Accordingly, there is a need in the art for an improved display for ophthalmic surgical consoles.

SUMMARY

In accordance with a first aspect of the disclosure, an ophthalmic surgical system includes a display device and a user interface. The display device generates a display on an image of a patient's eye comprising a plurality of non-overlapping display sectors. Each display sector displays one of a plurality of user-selectable surgical parameters. A user interface receives a user selection of one or more of the user-selectable surgical parameters to be displayed.

In accordance with another aspect of the disclosure, a method of displaying surgical parameters on an ophthalmic surgical system includes receiving a selection of at least two user-selectable surgical parameters. The method further includes generating a display on an image of a patient's eye comprising a plurality of non-overlapping display sectors. Each display sector displays one of the plurality of user-selectable surgical parameters

DETAILED DESCRIPTION

Figure 1:
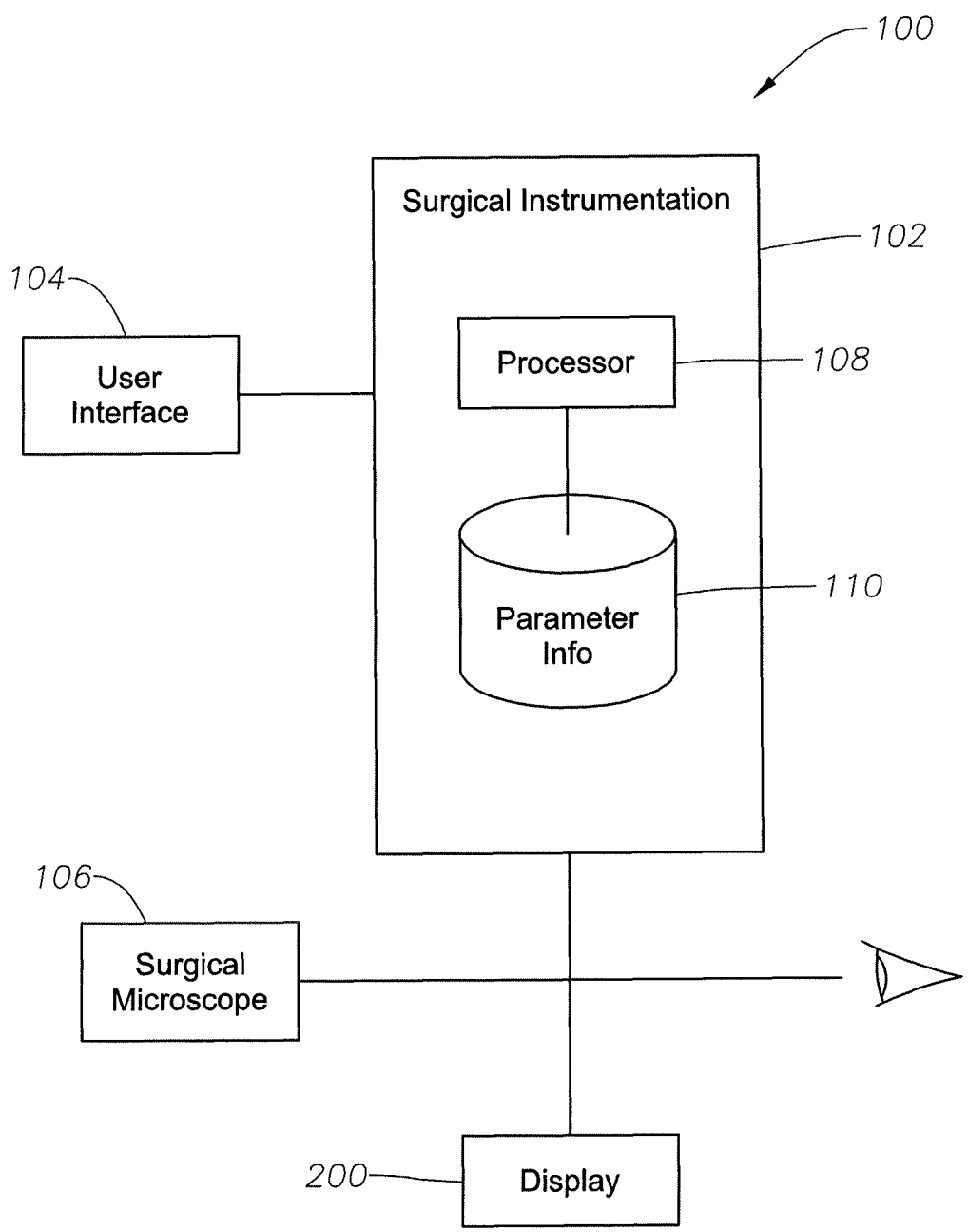
FIG. 1 illustrates an ophthalmic surgical system according to a particular embodiment of the present invention.

FIG. 1 illustrates an ophthalmic surgical system 100 according to a particular embodiment of the present invention. The system 100 includes surgical instrumentation 102, a user interface 104, and a surgical microscope 106. Surgical instrumentation 102 may include any type of component or machine used in ophthalmic surgery, including but not limited to handpieces, pneumatic systems, laser sources, illumination sources. Such components may be used in ophthalmic surgical techniques such as phacoemulsification, vitreoretinal surgery, laser refractive surgery, or any of the other various ophthalmic surgical methods known to one skilled in the art. The user interface 104 may include any kind of keyboard, switch, knob, pedal, button, pointing device, or other suitable component for receiving selections of surgical parameters from the user. The surgical microscope 106 may include any manner of optical or electronic device or collection of components providing a view of a patient's eye to the surgeon.

Surgical instrumentation 102 operates under the control of a processor 108; it also has memory 110 storing surgical parameter information. The processor 108 may be any microprocessor, microcontroller, programmable element, or other device or collection of devices for processing instructions for the control of surgical instrumentation 102. The processor 108 receives parameter selections from the user interface 104 and controls the operation of surgical parameters accordingly. The processor 108 also monitors surgical parameters during surgery. The memory 110 may be any suitable form of volatile or non-volatile information storage accessible by processor, including but not limited to optical, electronic, or magnetic media.

Various embodiments of surgical systems according to the present invention further include a display device 200. The display device 200 includes any suitable optical or electronic components or collection thereof capable of generating a visually-perceptible display of surgical parameters on an image of the patient's eye. For example, the display device 200 can project light onto a surface of the patient's eye to generate an image that is captured by the surgical microscope 106 along with the image of the eye. In another example, the display device 200 can project the display into an optical path of the surgical microscope 106 to produce the display over an image of the eye. Such embodiments may allow the display to be focused or magnified along with the image of the eye as well; alternatively, they may allow the display and the eye image to be focused or sized independently. In yet another example, the display device 200 can be incorporated into an eyepiece of the surgical microscope 106. The display device 200 may be configured to communicate with and/or share the processor 108 and/or the memory 110 in order to allow the surgical parameter display to be adjusted based on user selection of surgical parameters and variation of those parameters in real time during surgery.

Figure 2:
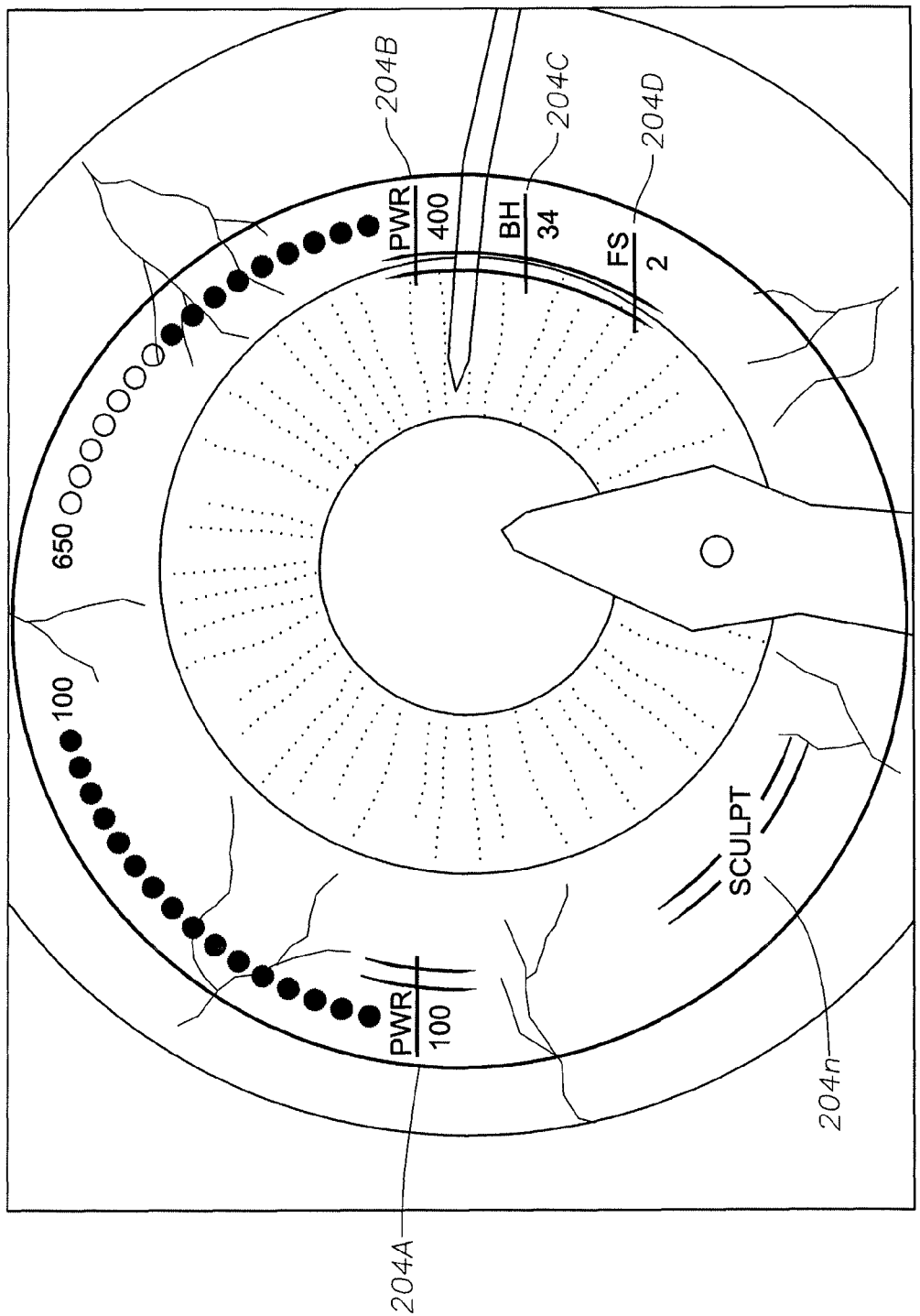
FIG. 2 illustrates an example display according to particular embodiments of the present invention.

FIG. 2 illustrates an example display 202 according to particular embodiments of the present invention. The display 202 includes a number of display sectors 204A, 204B, 204n, which will be generally referred to herein as display sectors 204. The term "display sectors" refers to the fact that these portions of the display fall within a sector of a circle centered at the center of display with the sector having a central angle less than 180 degrees. The display sectors are non-overlapping, which is to say that any quantitative portion of the display for any one surgical parameter does not extend circumferentially into another display sector 204 displaying a different surgical parameter. This includes any quantitative measurement scale, such as a scale indicating rotational alignment. However, purely visual elements unrelated to the surgical parameters or measurements, such as the arcs showing the inner edge of the display, may extend circumferentially without being considered "overlapping," so long as the quantitative display of the surgical parameters does not extend into another display sector 204.

The display 202 may be customized according to user-selectable surgical parameters. In particular embodiments, particular elements of the surgical parameter display may be further customized based on user preference. For example, the user may select from a variety of phacoemulsification and/or vitrectomy surgical parameters, including but not limited to power level, vacuum pressure for phacoemulsification, bottle height for irrigation solution, aspiration, footswitch position, phacoemulsification step and occlusion indicator. The user may also select minimum or maximum display values for ranged surgical parameters and displays with analog or digital values. Separating the display 202 into non-overlapping sectors 204 that can be individually selected and adjusted prevents the display 202 from becoming undesirably crowded, while still maintaining all of the information that the surgeon desires in an easily viewed format.

The surgical parameters can include any relevant operating parameter for the surgical instrumentation that is selected by the user and that is monitored or selected during surgery. The quantitative display of the parameter can be a number, a range, and on-off or other binary indicator, or any suitable visible element or combination of elements conveying relevant parameter information. In particular embodiments, real-time values can be shown on a variable gauge. Such gauges may include moving needles, bars with length that varies based on the value (e.g., vertical, horizontal, circumferential, radial), or bubble gauges, such as the ones illustrated in FIG. 2. Multiple display formats may also be user-selectable.

Colored elements may also be used in the display 202 to improve visibility, contrast, and the like. For example, a lighted green display taking the form illustrated in FIG. 2 would be easily visible when superimposed on the eye image. Gauges could also change color, such as changing to red when a parameter moves to an unacceptable range, when a laser source is active, or when some other notification to the surgeon might be required.

The display 202 may also include one or more axes to indicate directions on the display. For example, the display 202 may include the target axis for astigmatic correction when a toric lens is being implanted. In another example, the axis could indicate a desired incision line for lens implantation. Because the numerical and/or measurement scale displays of such lines do not extend circumferentially across sectors, they are also considered "non-overlapping" for purposes of this specification. Consequently, the incorporation of such visual elements should not be considered for purposes of determining the non-overlapping display sectors 204.

Figure 3:
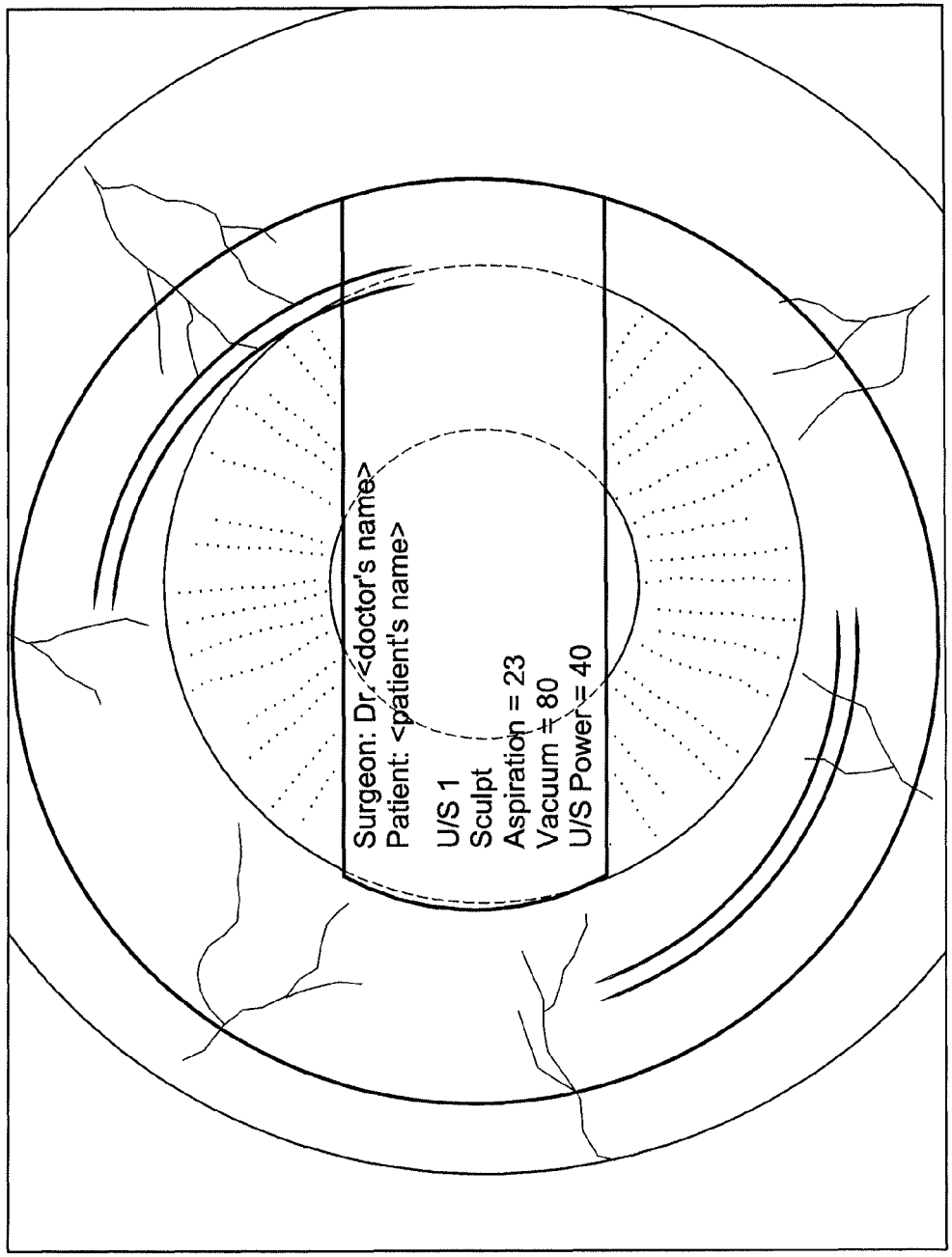
FIG. 3 shows an example selection screen that can be used in conjunction with various embodiments of an ophthalmic surgical system according to the present invention.

FIG. 3 shows an example selection screen 300 that can be used in conjunction with various embodiments of an ophthalmic surgical system 100 according to the present invention. The selection screen 300 confirms the procedure to be performed with the surgical instrumentation 102, the surgeon, and the patient on whom the procedure will be performed. The selection screen 300 also displays values for surgical parameters. The screen can allow selection of value ranges for the parameters, different parameters, etc., so that the user can appropriately configure the display 202 in advance of the surgical procedure.

Figure 4:
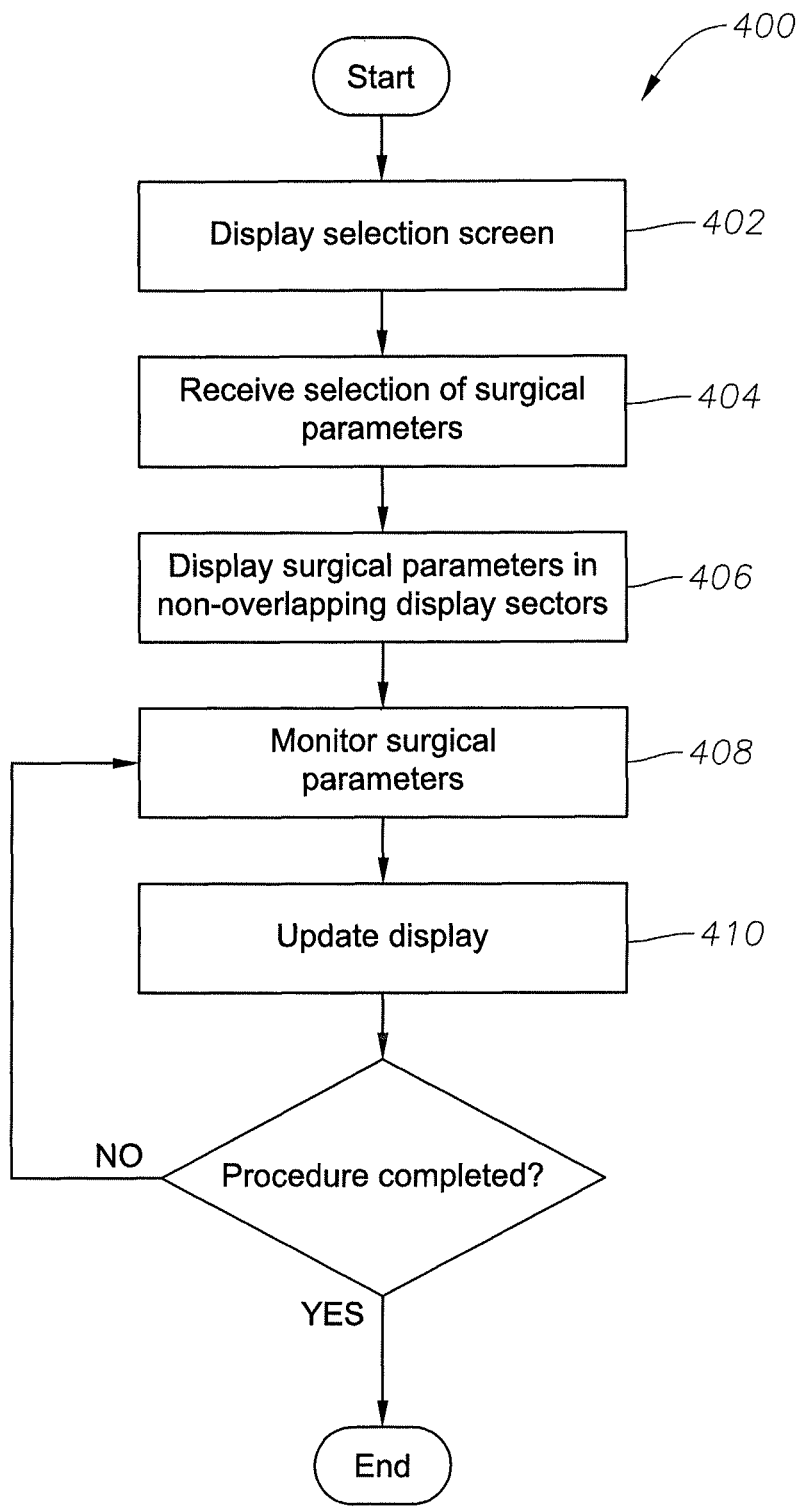
FIG. 4 is a flow chart showing an example method for displaying surgical parameters according to the present invention.

FIG. 4 is a flow chart showing an example method for displaying surgical parameters according to the present invention. At step 402, a selection screen is provided permitting selection of surgical parameters to be displayed. At step 404, a selection of surgical parameters to be displayed is received. The selection of surgical parameters may include, for example, which parameters will be displayed, what the display format will be, what range of various surgical parameters will be displayed, and the like. At step 406, the surgical parameters are displayed on non-overlapping display sectors. At step 408, the surgical parameters are monitored during the surgical procedure. At step 410, the display is updated based on a change in the surgical parameters. Steps 408 and 410 may be continuously performed until the surgical procedure is complete, as shown by decision step 412, at which time the method is at an end.

Embodiments described above illustrate but do not limit the invention. It should also be understood that numerous modifications and variations are possible in accordance with the principles of the present invention. Accordingly, the scope of the invention is defined only by the following claims.

What is claimed is:

1. A method of displaying surgical parameters for a phacoemulsification surgery system, comprising:
    receiving a selection of at least two user-selectable surgical parameters for a phacoemulsification surgery; and
    generating a display on an image of a patient's eye during the phacoemulsification surgery comprising a plurality of non-overlapping display sectors, each display sector displaying one of the plurality of user-selectable surgical parameters.

2. The method of claim 1, further comprising displaying a selection screen to the user.

3. The method of claim 1, wherein the step of generating the display further comprises displaying a target axis for astigmatic correction using a toric lens in the display on the image of the patient's eye.

4. The method of claim 1, further comprising determining a location for an incision and generating the display on the image of the patient's eye including an incision guide indicating the location for the incision.

5. The method of claim 1, wherein the user-selectable surgical parameters include a vacuum pressure.

6. The method of claim 1, wherein the user-selectable surgical parameters include a power level.

7. The method of claim 1, wherein the user-selectable surgical parameter indicates activity of a laser source.

8. The method of claim 1, wherein at least one of the user-selectable surgical parameters is displayed as a variable gauge.

9. The method of claim 1, wherein the display is generated by a display device, the display device generating the display as a lighted display.

10. The method of claim 1, wherein the display is generated by a display device, the display device projecting the display onto the patient's eye.

11. A method of displaying surgical parameters on an ophthalmic surgical system, comprising:
    receiving a selection of at least two user-selectable surgical parameters; and
    generating a display on an image of a patient's eye comprising a plurality of non-overlapping display sectors, each display sector displaying one of the plurality of user-selectable surgical parameters, wherein at least one of the user-selectable surgical parameters is displayed as a variable gauge and wherein the variable gauge is a bubble gauge.

12. The method of claim 11, further comprising displaying a selection screen to the user.

13. The method of claim 11, wherein the generated display further comprises a target axis for astigmatic correction using a toric lens.

14. The method of claim 11, further comprising determining a location for an incision and generating the display on the image of the patient's eye including an incision guide indicating the location for the incision.

15. The method of claim 11, wherein the user-selectable surgical parameters include a vacuum pressure.

16. The method of claim 11, wherein the user-selectable surgical parameters include a power level.

17. The method of claim 11, wherein the user-selectable surgical parameter indicates activity of a laser source.

18. The method of claim 11, wherein at least one of the user-selectable surgical parameters is displayed as a variable gauge.

* * * * *